United States Patent [19]

Kato et al.

[11] Patent Number: 4,874,956
[45] Date of Patent: Oct. 17, 1989

[54] METHOD AND APPARATUS FOR INSPECTING SEMICONDUCTOR DEVICES FOR THEIR BONDING STATUS

[75] Inventors: Toshihiro Kato, Chigasaki; Masamichi Shindo; Yoshihito Fukasawa, both of Yokohama, all of Japan

[73] Assignee: Kabushiki Kaisha Toshiba, Kawasaki, Japan

[21] Appl. No.: 177,412

[22] Filed: Apr. 4, 1988

[30] Foreign Application Priority Data

Apr. 14, 1987 [JP] Japan .................................. 62-89713

[51] Int. Cl.⁴ .............................................. G01N 21/86
[52] U.S. Cl. ...................................... 250/560; 250/561
[58] Field of Search ........................ 250/560, 561, 201; 356/376

[56] References Cited

U.S. PATENT DOCUMENTS

| | | | |
|---|---|---|---|
| 4,112,309 | 9/1978 | Nakazawa et al. | 250/560 |
| 4,115,650 | 5/1979 | Yasue et al. | 250/561 |
| 4,264,202 | 4/1981 | Gugliotta et al. | 250/561 |
| 4,736,108 | 4/1988 | Comstock et al. | 250/561 |
| 4,739,175 | 4/1988 | Tamura | 250/561 |

OTHER PUBLICATIONS

Laser Type Optical Switch/LZ series (catalog) Keyence Corp. Published: Sep. 1986, pp. 1–6.

*Primary Examiner*—David C. Nelms
*Attorney, Agent, or Firm*—Oblon, Spivak, McClelland, Maier & Neustadt

[57] ABSTRACT

An apparatus and a method for inspecting semiconductor devices, where a focused laser beam scans the semiconductor device, and the reflected beam thereof indicating height information of the reflection positions on the semiconductor device is detected for producing detected signals. The detected signals are compared with predetermined acceptance levels of height and distance.

11 Claims, 3 Drawing Sheets

METHOD AND APPARATUS FOR INSPECTING SEMICONDUCTOR DEVICES FOR THEIR BONDING STATUS

BACKGROUND OF THE INVENTION

1. Field of the Invention

This invention relates to an improved apparatus and a method for inspecting semiconductor devices, for example the bonding status of the semiconductor devices.

2. Description of the Prior Art

Conventionally, microscopes are widely used for inspecting the status of wire-bonding of semiconductor devices during manufacture. Recently, more complex image processing using TV cameras has been proposed for inspecting such semiconductor devices.

However, use of microscopes requires time consuming manual visual inspection. Thus, it is difficult to inspect all semiconductor devices. Accordingly, spot checks, namely checking some semiconductor devices from a lot, are performed. As a result, detection of all defective devices is not possible.

With more complex image processing techniques, the accuracy of detecting defective devices depends on the resolution of the TV camera. It is impossible to obtain "height information", namely three dimensional information, using a TV camera. Thus, it is necesary to combine images from a plurality of TV cameras to obtain such height information. This makes the image processing technique further complex and more expensive.

SUMMARY OF THE INVENTION

Accordingly, an object of this invention is to provide an improved apparatus and a method for inspecting the bonding of semiconductor devices at high speed and with high accuracy.

According to this invention, the foregoing object is attained by providing:

An apparatus for inspecting a semiconductor device comprising;

stage means for supporting the semiconductor device;

light source means for generating a focused light beam;

scanning means for scanning the focused light beam on the semiconductor device;

detecting means for sensing the light reflected from the semiconductor device, and producing detected output signals corresponding to the distance between the reflection point of the focused light beam and the light source means; and comparing means for comparing the level of the output signals with predetermined critical level. and A method for inspecting bonding in a semiconductor device, comprising the steps of:

preparing the semiconductor device on a stage means;

scanning a focused light beam, generated by a light source means, on the semiconductor device;

detecting the reflected light from the semiconductor device;

producing output signals corresponding to the distance between the reflection point of the focused light beam and the light source means; and comparing the level of the output signals with predetermined critical level.

Other object and advantages of the invention will become apparent from the following description.

BRIEF DESCRIPTION OF THE DRAWINGS

The accompanying drawings, which are incorporated and constitute a part of the specification, illustrate an embodiment of the invention, and together with the description serve to explain the principles of the invention, of the drawings.

DETAILED DESCRIPTION OF THE INVENTION

Figure 1:
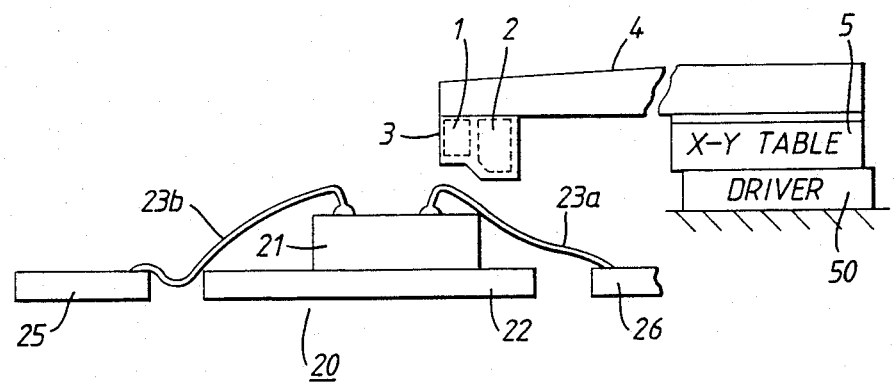
FIG. 1 is a side view of a semiconductor device aligned for inspection by an apparatus of this invention.

Reference now will be made to the drawings, wherein the same reference numerals designate corresponding parts throughout the drawings.

FIG. 1 shows one embodiment of this invention used in the inspection of the bonding status of a semiconductor device.

In FIG. 1, numeral 20 denotes a semiconductor device to be inspected. The semiconductor device 20 comprises a semiconductor pellet 21 mounted on a bed portion 22 of a lead frame, and fine wire leads 23a, 23b (e.g., 20 to 30 $\mu$m diameter) connected between the semiconductor pellet 21 and inner leads 25, 26. The semiconductor device 20 as shown is about half way through production. Namely, after inspection of the bonding status, if the device is favorably judged, it is molded with plastic material to complete the device. This semiconductor device is positioned on a stage means (not shown).

A sensor unit 3 includes light applying means 1 and detecting means 2. This sensor unit 3 is attched to a holding arm 4. The holding arm 4 is positioned on the X-Y table 5, and moved in accordance with the movement of the X-Y table 5. And the movement of the X-Y table 5 is controlled by a driver 50.

Figure 2:
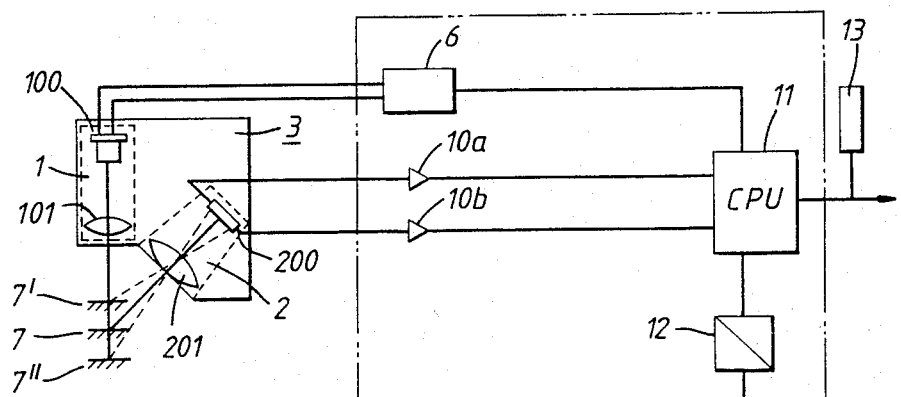
FIG. 2 is a schematic block diagram of apparatus of this invention.

FIG. 2 shows a block diagram of this invention. As shown in FIG. 2, light applying means 1 includes a laser device 100 and an optical lens 101. In this configuration, the laser device 100 emits laser beams of, e.g. 780 nm wavelength in response to a drive circuit 6. The laser beam is focused through the optical lens 101 to a spot of between 25 and 50 nm diameter, and is applied to the object 7 to be inspected, namely a semiconductor device. The detecting means 2 includes a detecting device 200, e.g., a CCD (Charge Coupled Device) line sensor, and an optical lens 201. In this configuration, the reflected light from the object 7 is focused by the optical lens 201, applied to the detecting device 200 and detected. The position where the reflected light is detected at the detecting device 200 is changed in accordance with the reflection point (7,7',7") of the object 7. More particularly, when the reflection point is higher (as shown at 7'), the reflected beam is detected at a lower position in the detecting device 200. Namely, in the case of a CCD line sensor, the corresponding CCD element located at a lower position is energized by the reflected laser beam to generate electric charges. Thus height information, or in other words, the distance between the reflection point of the laser beam and the light applying means 1, is obtained by detecting the position of the energized CCD element. As is well known, the generated charges are converted into electric output signals in a conventional way. It should be noted that the detecting device 200 should be large enough to detect the deflection of the reflected beam over a range to provide height information.

It is preferable that the optical lens 201 includes an autofocus mechanism. However, an autofocus mechanism is not essential to this invention, so a detailed autofocus mechanism is not illustrated. The output signal from the detecting device 200 is amplified by amplifiers 10a and 10b, and supplied to the CPU (Central Processing Unit) 11. The signal from the X-Y table 5, which represents the movement of the X-Y table 5 is encoded into digital signals by the processing circuit 12, and these signals are supplied to the CPU 11. In the CPU 11, the detected signals from the amplifiers 10a and 10b are synchronized with the encoded signals from the processing circuit 12. The CPU 11 controls the drive circuit 6 to control, for example the drive period of the laser device 100. The detected signals synchronized with the movement of the X-Y stage are displayed on a display 13.

The inspection of the semiconductor device is performed by scanning the focused laser beam.

Figure 3:
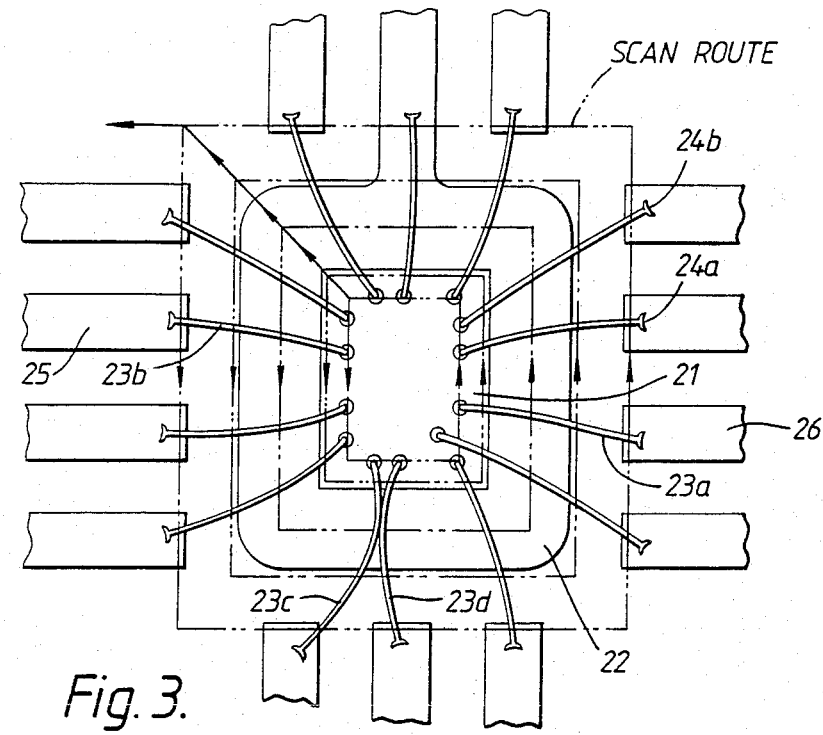
FIG. 3 is a plan view of a typical semiconductor device.
Figure 4:
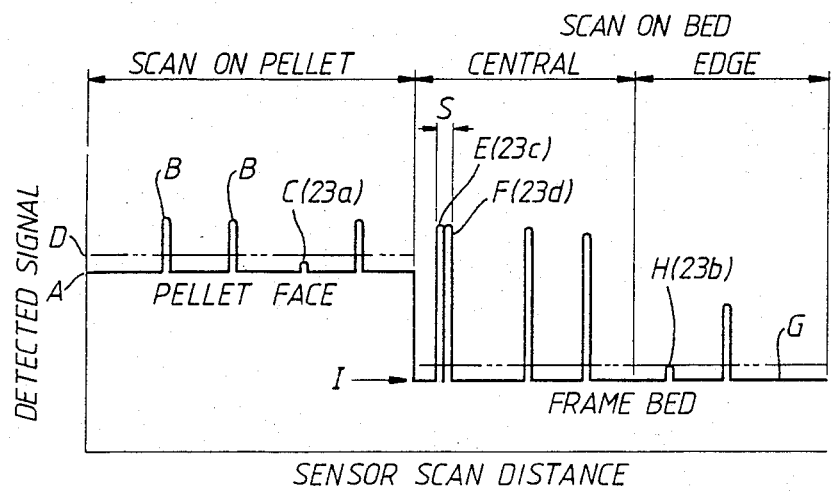
FIG. 4 is a diagram showing inspection results corresponding to the device of FIG. 3 generated by the apparatus of the invention.

FIG. 3 is a plan view of semiconductor device, and shows an example of the scanning of the laser beam. In FIG. 3, the dashed line shows an example of a scan route of the focused laser beam. First, the focused beam is scanned along the bonding pads on the semiconductor pellet 21. Next, it is scanned along the edge of the pellet 21. During the scanning of the semiconductor pellet 21, the status of the bonding wires against the semiconductor pellet 21 is inspected. Next, the focused beam is scanned on the bed portion 22, for example at the central portion and the edge portions thereof. Finally, the beam is scanned at the bonding portions of the leads 24(24a,24b... ). An example of the detected signals to be displayed on the display 13 is shown in FIG. 4. In FIG. 4, the axis of abscissas indicates the movement of the sensor or focused beam, and the axis of the ordinates indicates height information of the reflected point on the semiconductor device. To simplify the explanation, only the result of scanning at the edge of the semiconductor pellet 21 and at the central portion of the bed portion are shown in FIG. 4.

In FIG. 4, the level A corresponds the face level of the semiconductor pellet 21, and level I corresponds to the bed portion level of the frame. Level D is a predetermined critical level which represents the occurrence of contact between the bonding wire and the semiconductor pellet. Level G is also a predetermined critical level which represents the occurrence of contact between the bed portion and the bonding wire, and level S is a critical distance level which represents the occurrence of contact between the bonding wires near the scanning point. These critical levels are stored in the CPU 11.

In the scanning at the edge of the semiconductor pellet 21, the output level exceeds the critical level D when the bonding is satisfactorily done. However, when the bonding wire, such as bonding wire 23a shown in FIG. 1, contacts the edge of the semiconductor pellet 21, the corresponding output C does not reach the critical level D. Also, during the scanning at the central portion of the bed portion, if the wires are in contact with each other like wires 23c and 23d, the corresponding output signals E and F are also in contact. If the distance between the adjacent output signals is shorter than the critical distance level S, this indicates the occurrence of contact between the bonding wires near the scanning point. If the bonding wire (such as bonding wire 23b shown in FIG. 1) contacts the bed portion 22, the corresponding output H does not reach the critical level G.

Moreover, detected output signals which deviate from an ideal but do not indicate a bonding defect can be distinguished from those that do by use of signals corresponding to the critical levels.

As explained above, by comparing the output signals with the predetermined critical levels, it is possible to inspect the bonding status easily. In particular, in this invention the height information and the lateral information is obtained simultaneously. Thus the three dimensional inspection of the semiconductor device may be performed automatically at high speed.

Figure 5A:
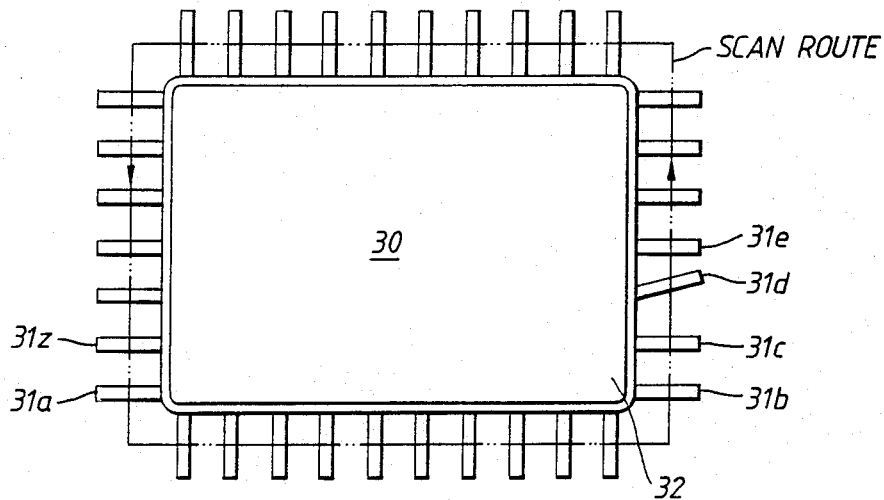
FIG. 5A is a plan view of another type of semiconductor device.
Figure 5B:
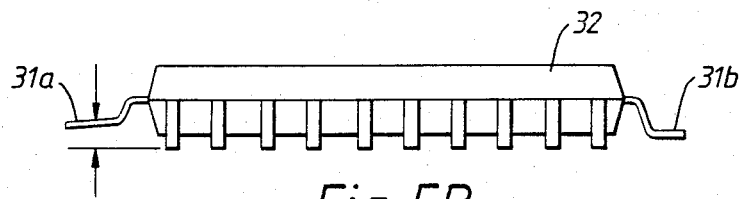
FIG. 5B is a side view of the device of FIG. 5A.

Next, another embodiment for inspecting the status of the outer leads of the semiconductor devices will be explained. FIG. 5A shows a plan view of a semiconductor device 30 to be inspected, which comprises a plastic body 32 and a plurality of outer leads 31(31a,31b... ). FIG. 5B shows a front view of the semiconductor device. For inspecting the status of the outer leads, the focused laser beam is scanned along the scan route in FIG. 5A shown by the dashed line.

Figure 6:
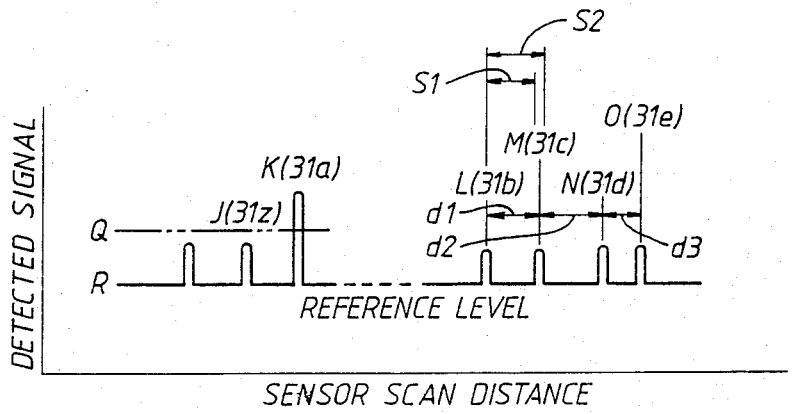
FIG. 6 is a diagram showing the inspection results corresponding the device in FIGS. 5A and 5B.

FIG. 6 shows an example of the output. In FIG. 6, the level R designates a reference level corresponding to, for example, the plane on which the semiconductor device is positioned. The levels S1 and S2 represent minimum and maximum critical levels of distance between the successive outer leads, respectively. In the scanning, if the outer lead is deformed upwardly, like outer lead 31a shown in FIG. 5B, the corresponding output K projects upwardly compared with the other output signals. If the output signal exceeds the critical level Q, the inspected device is judged as a defective one. In the event the outer lead is deformed or shifted laterally, like outer lead 31d as shown in FIG. 5A, the corresponding output N shifts toward the successive output O. In other words, the distance d3 between the output signals N and O is narrower then d3, and d2 is wider than d1. If the distance between the successive detected output signals is shorter than the minimum critical level S1 or wider than the maximum critical level S2, the inspected device is judged as a defective one.

As is apparent from the above description, by scanning the focused beam on each outer lead, the deformation of the outer leads both upwardly and laterally may be detected.

In the previous explanation, the focused beam is scanned by the movement of the sensor unit. However, it is possible to scan the focused beam by moving the semiconductor device. In this case the semiconductor device is positioned on a X-Y stage, and the sensor unit is fixed instead. Otherwise, the method is the same as the above description. Furthermore, it is possible to inspect the status of paste used to secure the semiconductor pellet to the bed portion by scanning the focused beam to the side face of the semiconductor pellet. Also, when the edge of the semiconductor pellet is reached during scanning, breakage of the edge can be also detected.

The present invention has been described with reference to a preferred embodiment. However, many other alternative embodiments will be obvious to those skilled in the art from the description.

What is claimed is:

1. An apparatus for inspecting the bonding status of semiconductor device comprising;
    stage means for supporting the semiconductor device;
    light source means for generating a focused light beam;
    scanning means for scanning the focused light beam on the semiconductor device;
    detecting means for sensing the light reflected from the semiconductor device, and producing detected output signals corresponding to the distance between the reflection point of the focused light beam and the light source means;
    critical level signal generating means for generating a predetermined critical level signal having a value such that a detected output signal less than said critical level signal will only be generated by a defectively bonded semiconductor device; and
    comparing means for comparing the level of the detected output signals with said predetermined critical level signal,
    whereby differences between said detected output signals and ideal output signals which are indicative of defective bonding in a defective semiconductor device may be distinguished from the differences which are not indicative of a defective semiconductor device.

2. The apparatus of claim 1, wherein the scanning means includes encoding means for generating encoded signals corresponding to the position of the focused beam on the semiconductor device.

3. The apparatus of claim 1, wherein the light source means includes a laser and lens means for focusing the light from the laser.

4. The apparatus of claim 1, wherein the scanning means includes means for moving the focused light beam on the semiconductor device.

5. The apparatus of claim 1, wherein the scanning means includes means for moving the semiconductor device for scanning the focused beam on the semiconductor device.

6. A method for inspecting the bonding status of semiconductor device, comprising the steps of:
    preparing the semiconductor device on a stage means;
    scanning a focused light beam, generated by a light source means, on the semiconductor device;
    detecting the reflected light from the semiconductor device;
    producing output signals corresponding to the distance between the reflection point of the focused light beam and the light source means;
    generating a predetermined critical level signal having a value such that a detected output signal less than said critical level signal will only be generated by a defective semiconductor device; and
    comparing the level of the detected output signals with said predetermined critical level signal,
    whereby differences between said detected output signals and ideal output signals which are indicative of defective bonding in a defective semiconductor device may be distinguished from the differences which are not indicative of a defective semiconductor device.

7. The method of claim 6, wherein the scanning of said focused light includes moving said semiconductor device.

8. The method of claim 6, wherein the semiconductor device includes a plurality of bonding wires, and the scanning of said focused light includes exposing each said bonding wire to the light beam.

9. The method of claim 6, wherein said semiconductor device comprises a plurality of outer leads, and the scanning of said focused light beam includes exposing each said outer lead to the light beam.

10. The method of claim 6 wherein said semiconductor device comprises a semiconductor chip mounted on a bed portion of a lead frame and having a plurality of bonding wires connected between inner leads of the semiconductor chip and bonding pads formed along the perimeter of the semiconductor chip, and wherein said scanning step comprises scanning around the perimeter of the semiconductor chip and around a perimeter of said bed portion, whereby said detected output signals correspond to the distance between said bonding wires and said light source means.

11. The method of claim 10, further comprising:
    scanning the focused light beam along the central portion between the perimeter of the semiconductor chip and the perimeter of the bed portion.

* * * * *